United States Patent
Yamaguchi et al.

(10) Patent No.: US 9,719,110 B2
(45) Date of Patent: Aug. 1, 2017

(54) METHOD OF INCREASING PRODUCTION OF AMORPHA-4,11-DIENE AND METHOD OF INCREASING PRODUCTION OF NATURAL RUBBER

(71) Applicants: SUMITOMO RUBBER INDUSTRIES, LTD., Kobe-shi, Hyogo (JP); OSAKA UNIVERSITY, Suita-shi, Osaka (JP)

(72) Inventors: Haruhiko Yamaguchi, Kobe (JP); Yukino Inoue, Kobe (JP); Keiji Takagi, Kobe (JP); Kazuhisa Fushihara, Kobe (JP); Toshiya Muranaka, Suita (JP); Keiko Suzuki, Suita (JP); Kanako Kobayashi, Suita (JP)

(73) Assignees: SUMITOMO RUBBER INDUSTRIES, LTD., Kobe-shi, Hyogo (JP); OSAKA UNIVERSITY, Suita-shi (JP)

( * ) Notice: Subject to any disclaimer, the term of this patent is extended or adjusted under 35 U.S.C. 154(b) by 0 days.

(21) Appl. No.: 14/942,476

(22) Filed: Nov. 16, 2015

(65) Prior Publication Data
US 2016/0153007 A1 Jun. 2, 2016

(30) Foreign Application Priority Data
Dec. 1, 2014 (JP) ................. 2014-242895

(51) Int. Cl.
*C12P 5/00* (2006.01)
*C12N 15/82* (2006.01)

(52) U.S. Cl.
CPC .......... *C12P 5/007* (2013.01); *C12N 15/8243* (2013.01); *C12P 5/002* (2013.01)

(58) Field of Classification Search
CPC ...................................................... C12P 5/007
See application file for complete search history.

(56) References Cited

PUBLICATIONS

Arsenault, P.R. et al., Curr. Med. Chem. (2008) vol. 15, No. 27: 2886 pp. 1-17.*
Kudakasseril, G.J. et al. Planta medica, 1987; 53(3): 280-284.*
Wu et al Nature Biotechnology Nov. 2007; V.24 n. 11 pp. 1441-1447.*
No art cited.*
Hao, B.-Z. and J.-L. Wu, "Laticifer Differentiation in *Hevea brasiliensis*: Induction by Exogenous Jasmonic Acid and Linolenic Acid," Annals of Botany (2000), vol. 85, pp. 37-43.

* cited by examiner

*Primary Examiner* — Russell Kallis
(74) *Attorney, Agent, or Firm* — Birch, Stewart, Kolasch & Birch, LLP

(57) ABSTRACT

The present invention provides a method of increasing production of amorpha-4,11-diene and a method of increasing production of natural rubber. The present invention relates to a method of increasing production of amorpha-4,11-diene which includes the step of attaching an enzyme inhibitor to *Arabidopsis thaliana* into which has been introduced a gene encoding amorphadiene synthase. The enzyme inhibitor inhibits at least one enzyme other than amorphadiene synthase, that catalyzes an enzymatic reaction in which farnesyl diphosphate acts as a substrate. The present invention also relates to a method of increasing production of natural rubber which includes the step of attaching an enzyme inhibitor to a rubber-producing plant. The enzyme inhibitor inhibits at least one enzyme other than enzymes involved in natural rubber synthesis, that catalyzes an enzymatic reaction in which farnesyl diphosphate acts as a substrate.

5 Claims, 2 Drawing Sheets

METHOD OF INCREASING PRODUCTION OF AMORPHA-4,11-DIENE AND METHOD OF INCREASING PRODUCTION OF NATURAL RUBBER

TECHNICAL FIELD

The present invention relates to a method of increasing production of amorpha-4,11-diene and a method of increasing production of natural rubber.

BACKGROUND ART

Artemisinin, an example of sesquiterpenes, has received attention as a compound having antimalarial activity.

Isoprenoid compound refers collectively to compounds biosynthesized from isopentenyl diphosphate (IPP) as a basic component. IPP is biosynthesized via the mevalonate pathway (MVA pathway) or the non-mevalonate pathway (MEP pathway). The sesquiterpene artemisinin is considered to be mainly biosynthesized from IPP derived from the MVA pathway in the cytoplasm via the intermediate metabolite farnesyl diphosphate (FPP).

The first reaction step of the artemisinin metabolic pathway is the biosynthesis of amorpha-4,11-diene by amorphadiene synthase (ADS) from FPP, an intermediate metabolite common to metabolic pathways of other compounds. Accordingly, increasing amorpha-4,11-diene biosynthesis is very beneficial for increasing artemisinin production and there is room for improvement by using metabolic engineering techniques.

Natural rubber, an example of polyisoprenoids, currently used in industrial rubber products is produced by growing *Hevea brasiliensis* (Para rubber tree) of the family Euphorbiaceae and collecting latex therefrom. *Hevea brasiliensis* has laticifer cells that biosynthesize and accumulate natural rubber (polyisoprenoid).

Although used in a wide variety of applications in large quantities as a raw material of rubber products, natural rubber is being collected substantially only from *Hevea brasiliensis*.

*Hevea brasiliensis*, however, is a plant that can grow only in limited areas such as in Southeast Asia or South America. Moreover, *Hevea brasiliensis* requires about seven years after planting to mature enough for rubber extraction, and the period during which natural rubber (isoprenoid) can be extracted is limited to 20 to 30 years.

As the demand for natural rubber is expected to rise in the future mainly in developing countries, there are concerns about the depletion of natural rubber resources. However, for the reason mentioned above, it is difficult to greatly increase production of natural rubber by planting *Hevea brasiliensis* as before. Thus, there is a need for a new method for increasing production of natural rubber.

For example, the following methods for improving the efficiency of natural rubber production in rubber-producing plants are known: ethylene or ethephon (2-chloroethylphosphonic acid) is applied to the trunk of a rubber-producing plant to prevent latex exuding from the latex vessels from coagulating at the cuts, thereby increasing the efficiency for collecting latex; and lanolin containing, for example, jasmonic acid or its precursor, linolenic acid, is applied to the trunk of a rubber-producing plant to promote laticifer differentiation, thereby increasing the density of latex vessels (Non-Patent Literature 1). These methods, however, do not directly act on the mechanism of natural rubber production and thus have limited effects on production increase.

CITATION LIST

Non Patent Literature

Non-Patent Literature 1: Hao et al., Annals of Botany, 2000, Vol. 85, pp. 37-43

SUMMARY OF INVENTION

Technical Problem

The present invention aims to solve the above problems and provide a method of increasing production of amorpha-4,11-diene and a method of increasing production of natural rubber.

Solution to Problem

It is considered that, in the natural rubber biosynthesis pathway, polymerization of isopentenyl diphosphate (IPP) using the intermediate metabolite FPP as a primer is repeated until finally natural rubber is biosynthesized.

As mentioned above, the first reaction step of the artemisinin metabolic pathway is the biosynthesis of amorpha-4,11-diene from FPP by amorphadiene synthase (ADS).

The intermediate metabolite FPP is also used in synthesis of many terpenoids other than the sesquiterpenoid artemisinin and the polyisoprenoid natural rubber, such as various sesquiterpenes, polyisoprenoids, triterpenes, sterols, and farnesyl groups of farnesylated proteins (see FIG. 1). FPP thus serves as a precursor in the biosynthesis of many terpenoids.

The present inventors focused on the fact that FPP serves as a precursor in the biosynthesis of many terpenoids and that FPP is the branch point. The inventors then arrived at the following technical idea: by inhibiting enzymes inducing pathways of undesired substances, it is possible to switch from the normal use of FPP in the biosynthesis of different terpenoids to the use of FPP in a specific biosynthetic pathway, and therefore to increase production of a desired substance.

After further intensive studies, the present inventors have found that the production of amorpha-4,11-diene can be increased in *Arabidopsis thaliana* into which has been introduced a gene encoding amorphadiene synthase, by inhibiting at least one enzyme other than amorphadiene synthase, that catalyzes an enzymatic reaction in which farnesyl diphosphate acts as a substrate. They have thereby completed the present invention.

Thus, one aspect of the present invention relates to a method of increasing production of amorpha-4,11-diene, the method including the step of attaching an enzyme inhibitor to *Arabidopsis thaliana* into which has been introduced a gene encoding amorphadiene synthase, the enzyme inhibitor inhibiting at least one enzyme other than amorphadiene synthase, that catalyzes an enzymatic reaction in which farnesyl diphosphate acts as a substrate.

After further intensive studies, the present inventors have found that the production of natural rubber can be increased in a rubber-producing plant by inhibiting at least one enzyme other than enzymes involved in natural rubber synthesis, that catalyzes an enzymatic reaction in which farnesyl diphosphate acts as a substrate. They have thereby completed the present invention.

Thus, a second aspect of the present invention relates to a method of increasing production of natural rubber, the method including the step of attaching an enzyme inhibitor to a rubber-producing plant, the enzyme inhibitor inhibiting at least one enzyme other than enzymes involved in natural rubber synthesis, that catalyzes an enzymatic reaction in which farnesyl diphosphate acts as a substrate. Preferably, the rubber-producing plant is at least one selected from the group consisting of *Hevea brasiliensis, Parthenium argentatum*, and *Taraxacum koksaghyz*.

Preferably, the at least one enzyme inhibited by the enzyme inhibitor includes squalene synthase.

Preferably, the enzyme inhibitor is squalestatin.

Preferably, the enzyme inhibitor is in the form of a solution in water or an aqueous medium, and a concentration of the enzyme inhibitor in the solution is 5 to 10 µmol/L.

Advantageous Effects of Invention

The method of increasing production of amorpha-4,11-diene of the first aspect of the present invention includes the step of attaching an enzyme inhibitor to *Arabidopsis thaliana* into which has been introduced a gene encoding amorphadiene synthase. The enzyme inhibitor inhibits at least one enzyme other than amorphadiene synthase, that catalyzes an enzymatic reaction in which farnesyl diphosphate acts as a substrate. The method thus can increase amorpha-4,11-diene production.

The method of increasing production of natural rubber of the second aspect of the present invention includes the step of attaching an enzyme inhibitor to a rubber-producing plant. The enzyme inhibitor inhibits at least one enzyme other than enzymes involved in natural rubber synthesis, that catalyzes an enzymatic reaction in which farnesyl diphosphate acts as a substrate. The method thus can increase natural rubber production.

DESCRIPTION OF EMBODIMENTS

Figure 1:
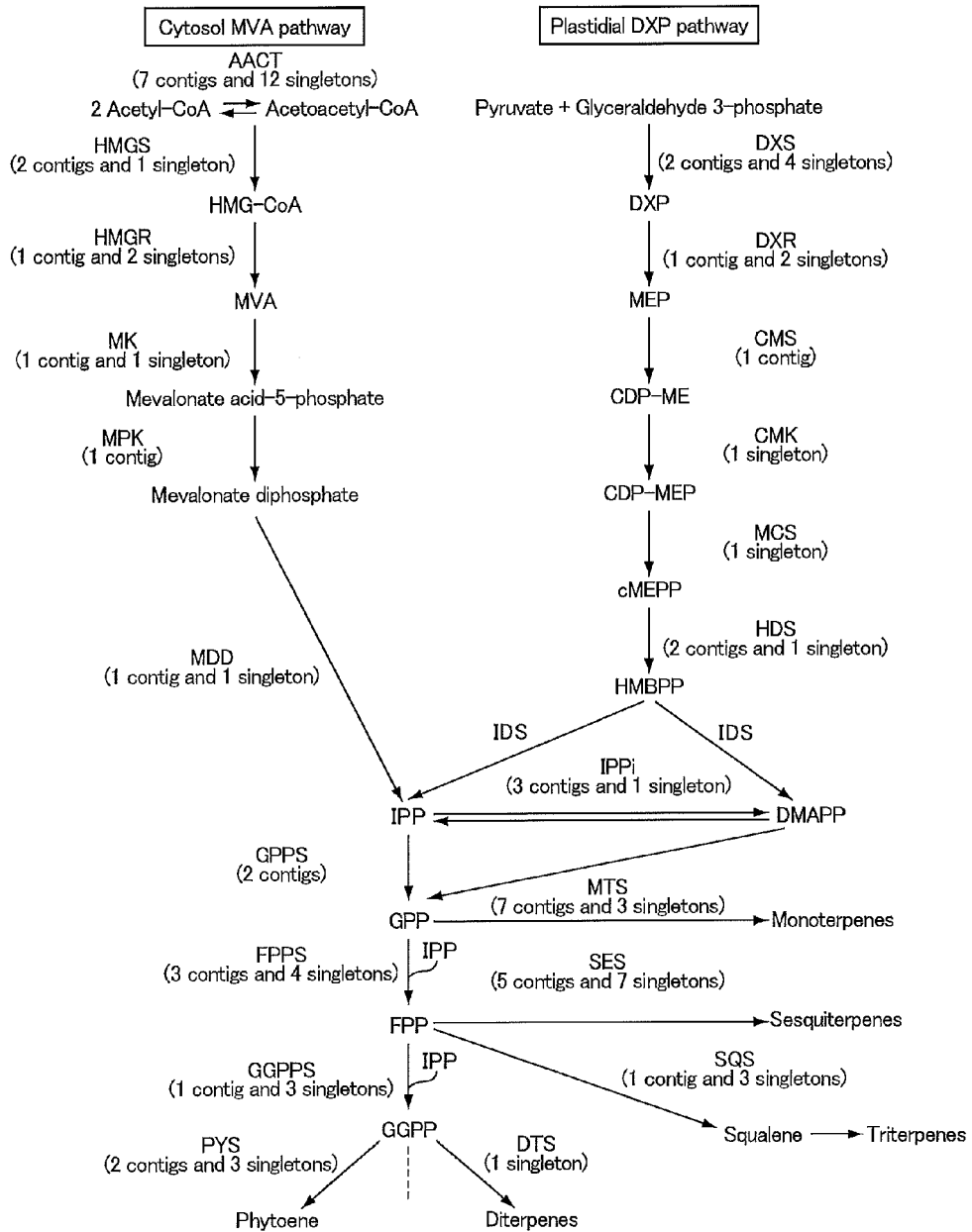
FIG. 1 is a schematic view showing part of polyisoprenoid biosynthesis pathways.

The first aspect of the present invention relates to a method of increasing production of amorpha-4,11-diene, which includes the step of attaching an enzyme inhibitor to *Arabidopsis thaliana* into which has been introduced a gene encoding amorphadiene synthase. The enzyme inhibitor inhibits at least one enzyme other than amorphadiene synthase, that catalyzes an enzymatic reaction in which farnesyl diphosphate acts as a substrate.

The term "amorphadiene synthase" as used herein means an enzyme that catalyzes an enzymatic reaction that synthesizes amorpha-4,11-diene using farnesyl diphosphate as a substrate.

The second aspect of the present invention relates to a method of increasing production of natural rubber, which includes the step of attaching an enzyme inhibitor to a rubber-producing plant. The enzyme inhibitor inhibits at least one enzyme other than enzymes involved in natural rubber synthesis, that catalyzes an enzymatic reaction in which farnesyl diphosphate acts as a substrate.

The term "natural rubber" as used herein means a polymer having isoprene units ($C_5H_8$).

The content of 1,4-cis isoprene units in natural rubber is preferably 10 mol % or more, more preferably 30 mol % or more, still more preferably 60 mol % or more, particularly preferably 90 mol % or more, most preferably 98 mol % or more. The upper limit of the content of 1,4-cis units is not particularly limited.

The content of 1,4-cis units can be determined by NMR.

The natural rubber preferably has a weight average molecular weight (Mw) of 1,000 or more, more preferably 10,000 or more, still more preferably 100,000 or more, particularly preferably 1,000,000 or more. If the Mw is less than 1,000, the natural rubber tends to be difficult to use as rubber.

Moreover, the upper limit of the weight average molecular weight is not particularly limited.

The Mw of natural rubber can be determined by gel permeation chromatography (GPC) relative to polystyrene standards or the like.

In the first aspect of the present invention, the plant *Arabidopsis thaliana* into which has been introduced a gene encoding amorphadiene synthase (ADS) is used.

Although the gene encoding ADS may be of any origin, the gene is preferably derived from a plant, more preferably from a plant of the genus *Artemisia*, still more preferably from *Artemisia annua*.

The gene encoding ADS can be introduced to *Arabidopsis thaliana* by any method. Known methods can be used.

In the second aspect of the present invention, a rubber-producing plant is used.

The rubber-producing plant may be any plant that can produce natural rubber. Examples include plants of the genus *Hevea*, such as *Hevea brasiliensis*; plants of the genus *Sonchus*, such as *Sonchus oleraceus, Sonchus asper*, and *Sonchus brachyotus*; plants of the genus *Solidago*, such as *Solidago altissima, Solidago virgaurea* subsp. *asiatica, Solidago virgaurea* subsp. *leipcarpa, Solidago virgaurea* subsp. *leipcarpa f. paludosa, Solidago virgaurea* subsp. *gigantea*, and *Solidago gigantea Ait.* var. *leiophylla* Fernald; plants of the genus *Helianthus*, such as *Helianthus annuus, Helianthus argophyllus, Helianthus atrorubens, Helianthus debilis, Helianthus decapetalus*, and *Helianthus giganteus*; plants of the genus *Taraxacum*, such as *Taraxacum, Taraxacum venustum* H. Koidz, *Taraxacum hondoense* Nakai, *Taraxacum platycarpum* Dahlst, *Taraxacum japonicum, Taraxacum officinale* Weber, and *Taraxacum koksaghyz*; plants of the genus *Ficus*, such as *Ficus carica, Ficus elastica, Ficus pumila* L., *Ficus erecta* Thumb., *Ficus ampelas* Burm. f., *Ficus benguetensis* Merr., *Ficus irisana* Elm., *Ficus microcarpa* L.f., *Ficus septica* Burm. f., and *Ficus benghalensis*; plants of the genus *Parthenium*, such as *Parthenium argentatum, Parthenium hysterophorus*, and *Parthenium hysterophorus*; and *Lactuca serriola*. Among these, the rubber-producing plant is preferably at least one selected from the group consisting of plants of the genera *Hevea, Parthenium*, and *Taraxacum*, and more preferably from the group consisting of *Hevea brasiliensis, Parthenium argentatum*, and *Taraxacum koksaghyz*.

In the first aspect of the present invention, the enzyme(s) to be inhibited by the enzyme inhibitor may be any enzyme other than amorphadiene synthase, that catalyzes an enzymatic reaction in which farnesyl diphosphate acts as a substrate. Examples include squalene synthase (SQS).

The enzyme inhibitors usable in the first aspect of the present invention are not particularly limited as long as the enzyme inhibitors inhibit at least one enzyme other than amorphadiene synthase, that catalyzes an enzymatic reaction in which farnesyl diphosphate acts as a substrate. Specifically, any enzyme inhibitor that can inhibit the enzyme exemplified above can be used, and examples include squalestatin. In particular, enzyme inhibitors capable of inhibiting squalene synthase are preferred because they are highly effective in increasing production of amorpha-4,11-diene. Among the above-mentioned inhibitors, squalestatin is included in the enzyme inhibitors capable of inhibiting squalene synthase. In particular, squalestatin is preferred because it is highly effective in increasing production of amorpha-4,11-diene.

In the second aspect of the present invention, the enzyme(s) to be inhibited by the enzyme inhibitor may be any enzyme other than enzymes involved in natural rubber synthesis, that catalyzes an enzymatic reaction in which farnesyl diphosphate acts as a substrate. Examples include squalene synthase (SQS).

The enzyme inhibitors usable in the second aspect of the present invention are not particularly limited as long as the enzyme inhibitors inhibit at least one enzyme other than enzymes involved in natural rubber synthesis, that catalyzes an enzymatic reaction in which farnesyl diphosphate acts as a substrate. Specifically, any enzyme inhibitor that can inhibit the enzyme exemplified above can be used, and examples include squalestatin. In particular, enzyme inhibitors capable of inhibiting squalene synthase are preferred because they are highly effective in increasing production of natural rubber. Among the above-mentioned inhibitors, squalestatin is included in the enzyme inhibitors capable of inhibiting squalene synthase. In particular, squalestatin is preferred because it is highly effective in increasing production of natural rubber.

The reason that the inhibition of squalene synthase, that is, the use of an enzyme inhibitor capable of inhibiting squalene synthase, is highly effective in increasing production of amorpha-4,11-diene or natural rubber is assumed as follows. The inhibition of the enzymes mentioned above can increase the amount of FPP flowing into the pathway of biosynthesis of a desired substance. In the case of the inhibition of squalene synthase, not only can the above effect be exerted, but also the activity of 3-hydroxy-3-methylglutaryl CoA reductase (HMGR), which is a rate-limiting enzyme in the IPP-supplying MVA pathway, can be enhanced by the feedback control mechanism of the plant, resulting in increased biosynthesis of IPP monomer and, therefore, increased biosynthesis of FPP. Presumably, these effects are synergistically combined to produce a significant effect in increasing production of amorpha-4,11-diene or natural rubber.

In the first and second aspects of the present invention, the enzyme inhibitor is preferably in the form of a solution in water or an aqueous medium. This allows the enzyme inhibitor to easily attach to the plant and to effectively act thereon.

The aqueous medium may be any aqueous medium, and examples include alcohols such as ethanol, methanol, and isopropyl alcohol, ketones such as acetone and ethyl methyl ketone, and dimethyl sulfoxide.

The solvent for dissolving the enzyme inhibitor is preferably water, which has a low impact on plants. For enzyme inhibitors poorly soluble in water, solvents such as ethanol or dimethyl sulfoxide may be used.

The concentration of the enzyme inhibitor (concentration of the enzyme inhibitor in the enzyme inhibitor solution) to be attached to the plant is preferably 3 to 10 µmol/L, more preferably 5 to 10 µmol/L. When the concentration is adjusted in the range described above, the production of amorpha-4,11-diene or natural rubber can be increased while reducing the adverse effects of the enzyme inhibitor on plant growth. If the concentration is less than 3 µmol/L (preferably less than 5 µmol/L), although growth inhibition is less likely to occur, the effect of increasing production of amorpha-4,11-diene or natural rubber may be insufficient. Conversely, if the concentration is greater than 10 µmol/L, although the effect of increasing production of amorpha-4,11-diene or natural rubber is high, significant growth inhibition of the plant may occur.

In particular, when squalestatin is used as the enzyme inhibitor and the concentration of the enzyme inhibitor is 5 to 10 µmol/L, the growth inhibition of the plant can be minimized, and the effect of increasing production of amorpha-4,11-diene or natural rubber can be suitably achieved.

In the first and second aspects of the present invention, the enzyme inhibitor may be attached to the plant by any method that allows the enzyme inhibitor to be attached to the plant so that the enzyme inhibitor contacts the plant. Examples of such a method include application of the enzyme inhibitor to the plant, and spraying of the enzyme inhibitor onto the plant. Specifically, for example, the enzyme inhibitor solution may be applied to the plant with, for example, a brush, or may be sprayed with a spray or the like.

Other methods include culturing the plant in a medium containing the enzyme inhibitor.

As the plant, cells of the plant may be used.

The enzyme inhibitor may be attached to any part of the plant, such as the trunk, stem, root, leaf, leafstalk, bud, petal, cotyledon, hypocotyl, or anther of the plant. Among these, the trunk, stem, and root are preferred, and the trunk and stem are more preferred, because then the effect of the present invention can be suitably achieved. Since the trunk and stem are rich in rubber-producing laticifer tissues, the effect of increasing rubber production can be suitably achieved.

First, the application or spraying of the enzyme inhibitor onto the plant will be described.

The amount of the enzyme inhibitor to be attached per plant is not particularly limited, and may be appropriately selected according to the weight of the plant or other factors.

The concentration of the enzyme inhibitor to be attached to the plant is as described above.

If the rubber-producing plant is a woody plant, it is preferred that, before the step of attaching the enzyme inhibitor to the rubber-producing plant, the cork layer of the rubber-producing plant is peeled off and the enzyme inhibitor is then attached to the peeled portion. Since the hard cork layer covers the surface of the rubber-producing plant, peeling the cork layer allows the enzyme inhibitor to easily reach tissues under the cork layer, thereby enhancing the production increase effect.

The cork layer refers to a layer which is located in the outer bark of a rubber-producing plant and is present outside the laticifer cells and tissues formed from laticifer cells. The portion of the trunk or stem from which the cork layer is to be peeled off may be any portion as long as the enzyme inhibitor can be attached to the portion to produce the production increase effect. Preferably, the portion is near where latex is recovered by tapping. Moreover, the thickness of the portion to be peeled off may be any thickness as long as the cork layer can be peeled off without damaging the laticifer cells and tissues formed from laticifer cells. The thickness is, for example, 0.1 to 10 mm, preferably 0.5 to 8 mm, still more preferably 3 to 6 mm.

The cork layer may be peeled off by any method, and conventional methods for peeling off the bark or the like can be used. For example, a method may be used involving peeling off the cork layer by partially cutting the trunk or stem with a knife or the like. Moreover, the time to peel and the number of portions to be peeled are not particularly limited as long as the production increase effect can be achieved. These conditions maybe appropriately chosen in view of, for example, the type and the concentration of the active ingredient of the enzyme inhibitor, the attachment method, or the age and the type of the plant.

If the rubber-producing plant is an herbaceous plant, since it has no cork layer, the enzyme inhibitor may be directly attached to an attachment part (e.g., the stem).

The enzyme inhibitor may be attached to the plant at any time. In order to reduce growth inhibition of the plant, it is desirable to start the attachment of the enzyme inhibitor a few days before a desired substance is collected, rather than to attach the enzyme inhibitor constantly during the growth of the plant. The attachment may be started at any time. Since it is believed that a certain amount of time is required after the attachment before the effect can be obtained, the attachment is preferably started three days before, more preferably five days before, still more preferably one week before the collection of a desired substance.

If the rubber-producing plant is a woody plant, a groove-like cut may be made with a knife or the like (i.e., tapping), and natural rubber can be recovered as an exudate from the cut latex vessels. If the rubber-producing plant is an herbaceous plant, a cut may be made in the stem or root (i.e., tapping), and natural rubber can be recovered as an exudate from the cut latex vessels. Alternatively, the plant may be freeze-dried and then ground with a mortar, and natural rubber can be recovered from the ground product using an organic solvent.

Next, the culture of the plant in a medium containing the enzyme inhibitor will be described.

The culture may be performed under any conditions that allow the plant to produce amorpha-4,11-diene or natural rubber. Conventional media for culturing plants or plant cells may be used. Specific examples include basal media such as White medium, Heller medium, Schenk and Hildebrandt (SH) medium, Murashige and Skoog (MS) medium, Linsmaier and Skoog (LS) medium, Gamborg medium, B5 medium, MB medium, and WP medium (medium for woody plants). The enzyme inhibitor may be added to these media. The medium is preferably liquid in order to suitably attach the enzyme inhibitor to the plant.

The concentration of the enzyme inhibitor in the medium is the same as described above for the concentration of the enzyme inhibitor to be attached to the plant. With such a concentration, the production of amorpha-4,11-diene or natural rubber can be increased while reducing the adverse effects of the enzyme inhibitor on plant growth.

The culture temperature is preferably 0° C. to 50° C., more preferably 10° C. to 40° C., still more preferably 20° C. to 35° C., depending on the type of plant or plant cell. The pH is preferably 3 to 11, more preferably 4 to 10, still more preferably 5 to 9.

The culture may be carried out batchwise or in a continuous fashion using a bioreactor. Specific examples of the culture method include shake culture and rotation culture. Amorpha-4,11-diene or natural rubber can be accumulated in the cells, or may be produced and accumulated in the culture supernatant.

In the case of obtaining amorpha-4,11-diene or natural rubber from the cultured plants or plant cells, the plants or plant cells may be recovered by, for example, centrifugation and then disrupted, and amorpha-4,11-diene or natural rubber can be extracted from the homogenate using a solvent such as n-hexane. The solvent extraction may be appropriately combined with a known purification process, such as chromatography.

In the case of obtaining amorpha-4,11-diene or natural rubber from the culture supernatant, the plants or plant cells may be removed by, for example, centrifugation, and then amorpha-4,11-diene or natural rubber can be extracted from the resulting supernatant using a solvent such as n-hexane. The solvent extraction may be appropriately combined with a known purification process, such as chromatography.

EXAMPLES

The present invention will be described in more detail with reference to, but not limited to, examples below.

Example 1

The following experiment was performed to confirm that the attachment of the enzyme inhibitor squalestatin (squalene synthase inhibitor) had the effect of increasing production of amorpha-4,11-diene on 35S:ADS *A. thaliana*, which is an *Arabidopsis thaliana* into which had been introduced a gene encoding amorphadiene synthase (ADS).

The 35S:ADS *A. thaliana* is *Arabidopsis thaliana* in which a gene encoding ADS derived from *Artemisia annua* is overexpressed. It is properly managed as 433 7-5 line in Cell Technology Laboratory, Division of Advanced Science and Biotechnology, Graduate School of Engineering, Osaka University.

In order to sterilize 35S:ADS *A. thaliana* seeds, the seeds were immersed in a seed sterilization water (0.25% sodium hypochlorite solution, 1% SDS) for 20 minutes and then washed with sterilized water four times.

The seeds were plated on MS agar medium (Murashige and Skoog medium, including 4.4 g/L vitamins, 10 g/L sucrose, and 10 g/L agar) set to a pH of 5.8.

The plating was followed by vernalization for two or more days at 4° C. Thereafter, the seeds were cultured at 23° C. under long day conditions (16 hours light/8 hours dark) for seven days.

The resulting *Arabidopsis thaliana* seedlings were transferred to MS liquid media supplemented with squalestatin (SQS inhibitor) at squalestatin concentrations of 0, 1, 3, 5, 10, and 15 µmol/L, followed by further culturing for seven days with shaking at 23° C. under long day conditions (16 hours light/8 hours dark).

After the seven-day shake culture, the wet weight of the *Arabidopsis thaliana* plants thus grown was measured, and then the effects on growth inhibition were compared.

Amorpha-4,11-diene was extracted from the *Arabidopsis thaliana* plants by the following procedure. About 100 mg (wet weight) of *Arabidopsis thaliana* plants was placed in a mortar, to which was added about 5 mL of n-hexane. After 100 µL of a n-tetradecane solution was added as an internal standard, the mixture was subjected to grinding and extraction. The extract was once recovered, and the residue was combined with another 5 mL of fresh n-hexane, followed by grinding and extraction. The extract from the second extraction was combined with that from the first extraction. This cycle of operation was repeated twice. The resulting extract was passed through an anhydrous sodium sulfate column.

The eluate from the column was concentrated under reduced pressure to about 1 mL using a rotary evaporator, and then dried to a solid with a nitrogen blowing concentrator.

The dried solid was finally combined with 1 mL of n-hexane to prepare a sample for GC-MS analysis.

The GC-MS analysis was performed with a JMS-SUN200 mass spectrometer (JEOL) and a gas chromatograph (6890 series GC system: Agilent Technologies).

The gas chromatography was performed using a deactivated silica capillary tube (GL Sciences) as a guard column and HP-5MS (Agilent Technology J & W) as a capillary column.

Figure 2:
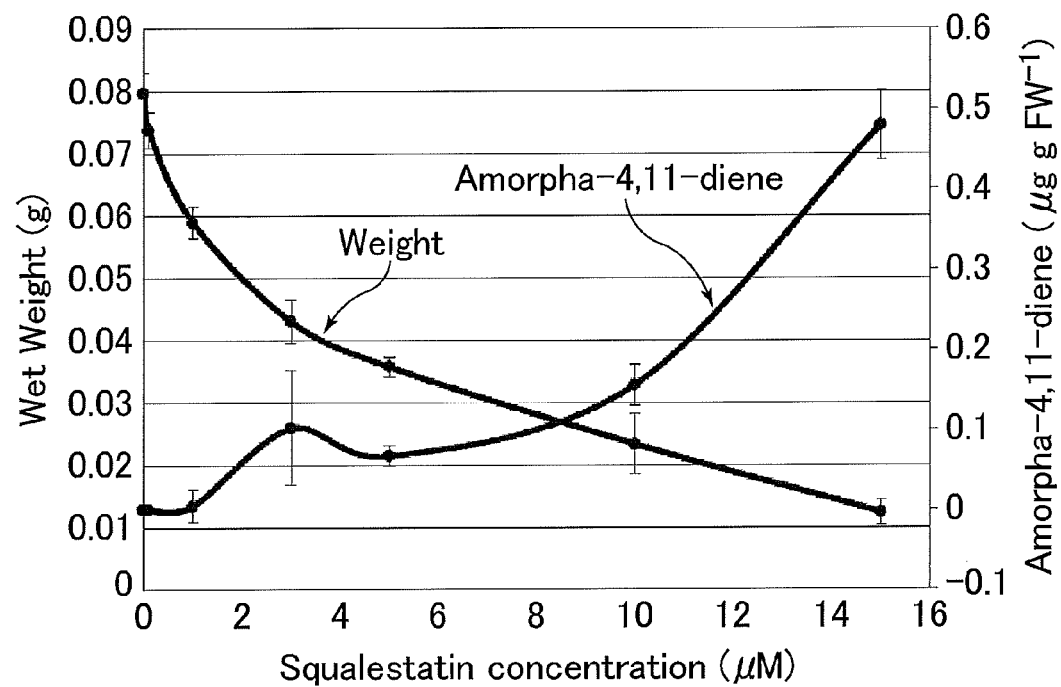
FIG. 2 is a schematic view showing an example of the wet weight of plants and the amount of amorpha-4,11-diene at various squalestatin concentrations.

FIG. 2 shows the wet weight of plants and the amount of amorpha-4,11-diene at various squalestatin concentrations.

FIG. 2 demonstrates that the treatment with 3 µmol/L or more of squalestatin resulted in an increase in the amount of amorpha-4,11-diene inside *Arabidopsis thaliana* plants. From the results of the wet weight of plants, on the other hand, the treatment with more than 10 µmol/L of squalestatin caused significant growth inhibition.

Comparative Example

Instead of squalene synthase (SQS), squalene epoxidase (SQE), which is located one step downstream of SQS, was inhibited, and then the effect of increasing production of amorpha-4,11-diene was evaluated.

The same procedure was followed as in Example 1, except that *Arabidopsis thaliana* seedlings obtained as described in Example 1 were transferred to MS liquid media supplemented with terbinafine (SQE inhibitor) at terbinafine concentrations of 0, 1, 3, and 5 µmol/L.

The treatment with terbinafine resulted in very little increase in the production of amorpha-4,11-diene in *Arabidopsis thaliana*. In the case of the treatment with 5 µmol/L of terbinafine, an accumulation of only about 0.004 µg gFW$^{-1}$ (a tenth or less of the amount obtained by treatment with the same concentration of squalestatin) was observed.

Example 2

The following experiment was performed to confirm that the attachment of the enzyme inhibitor squalestatin (squalene synthase inhibitor) to the rubber-producing plant *Taraxacum koksaghyz* had the effect of increasing production of natural rubber.

*Taraxacum koksaghyz* seeds were vernalized for two or more days at 4° C. and then planted in soil.

After planted in soil, the seeds were grown at 25° C. under 12 h light/12 h dark conditions for five months.

Squalestatin was dissolved at a concentration of 10 µmol/L in 0.1% dimethyl sulfoxide (DMSO) to prepare a squalestatin solution. Two of the thus grown *Taraxacum koksaghyz* plants were each sprayed with 50 mL of the squalestatin solution once a day for four days using a spray.

As a comparative example, another two *Taraxacum koksaghyz* individuals were sprayed with 50 mL of a 0.1% dimethyl sulfoxide (DMSO) solution without squalestatin once a day for four days using a spray.

On day 5 after initiation of the treatment, latex was recovered from the *Taraxacum koksaghyz* roots and immersed in ethanol for five hours to solidify natural rubber.

The solidified natural rubber was dried at room temperature for three days. Thereafter, the dry weight was measured, and the results were compared.

Table 1 shows that the amount of natural rubber recovered from *Taraxacum koksaghyz* treated with squalestatin increased 2.5 times as compared to *Taraxacum koksaghyz* not treated with squalestatin. It should be noted that each result shown in Table 1 represents the average of the measurements of two individuals.

The weight average molecular weight (polystyrene equivalent Mw) of the rubber obtained in Example 2 was determined under the following conditions (1) to (7) by gel permeation chromatography (GPC). The Mw was about 2,470,000 (see Table 1). This seems to indicate that there was no change in molecular weight as compared to the rubber obtained without treatment with squalestatin (Mw: about 2,440,000), and the enzyme inhibitor affected only the yield.

(1) Device: HLC-8020 available from Tosoh Corporation
(2) Separation column: GMH-XL available from Tosoh Corporation
(3) Measurement temperature: 40° C.
(4) Carrier: tetrahydrofuran
(5) Flow rate: 0.6 mL/min
(6) Detector: differential refractometer, UV (215 nm)
(7) Molecular weight standards: polyisoprene standards, polystyrene standards

TABLE 1

|  | Squalestatin treatment concentration (µmol/L) | Rubber dry weight (mg) | Rubber molecular weight (Mw) |
|---|---|---|---|
| Comparative Example | 0 | 1.7 | 2444727 |
| Example 2 | 10 | 4.2 | 2469495 |

The invention claimed is:

1. A method of increasing production of natural rubber, the method comprising the step of attaching an enzyme inhibitor to a rubber-producing plant,
    the enzyme inhibitor inhibiting at least one enzyme other than enzymes involved in natural rubber synthesis, that catalyzes an enzymatic reaction in which farnesyl diphosphate acts as a substrate.

2. The method of increasing production of natural rubber according to claim 1,
    wherein the at least one enzyme inhibited by the enzyme inhibitor comprises squalene synthase.

3. The method of increasing production of natural rubber according to claim 1,
    wherein the enzyme inhibitor is squalestatin.

4. The method of increasing production of natural rubber according to claim 1,
    wherein the enzyme inhibitor is in the form of a solution in water or an aqueous medium, and
    a concentration of the enzyme inhibitor in the solution is 5 to 10 µmol/L.

5. The method of increasing production of natural rubber according to claim 1,
    wherein the rubber-producing plant is at least one selected from the group consisting of *Hevea brasiliensis*, *Parthenium argentatum*, and *Taraxacum koksaghyz*.

* * * * *